United States Patent [19]
Garito et al.

[11] Patent Number: 5,741,250
[45] Date of Patent: *Apr. 21, 1998

[54] ELECTROSURGICAL INSTRUMENT FOR EAR SURGERY

[76] Inventors: Jon C. Garito; Alan G. Ellman, both of 1135 Railroad Ave., Hewlett, N.Y. 11557

[*] Notice: The term of this patent shall not extend beyond the expiration date of Pat. No. 5,571,101.

[21] Appl. No.: 593,011

[22] Filed: Jan. 29, 1996

[51] Int. Cl.$^6$ .......................... A61B 17/38; A61B 17/36
[52] U.S. Cl. .................. 606/45; 607/98; 607/115; 607/145
[58] Field of Search .......................... 607/2, 98, 99, 607/115, 116, 137, 145, 146, 149, 150, 151; 606/45

[56] References Cited

U.S. PATENT DOCUMENTS

| | | | |
|---|---|---|---|
| 4,892,105 | 1/1990 | Prass | 607/116 |
| 4,962,766 | 10/1990 | Herzon | 607/150 |
| 5,035,695 | 7/1991 | Weber, Jr. et al. | 606/45 |
| 5,267,994 | 12/1993 | Gentelia et al. | 606/45 |
| 5,403,311 | 4/1995 | Abele et al. | 606/45 |
| 5,571,101 | 11/1996 | Ellman et al. | 606/45 |

*Primary Examiner*—William E. Kamm
*Assistant Examiner*—Carl H. Layno

[57] ABSTRACT

An electrode for use in an electrosurgical aural procedure known as a myringotomy for incising tissue of the tympanic membrane. In a preferred embodiment, the electrode is characterized by a bare active tip portion terminating a colinear electrically-insulated electrode shaft offset at an angle from a handle. The tissue incising is effected with the bare tip at a depth stopped by a shoulder between the bare tip and the adjacent portions of the electrode shaft. The electrical insulation prevents accidental burns to the patient and allows the physician to use these insulated parts to help position and guide the active tip portion during the surgical procedure.

11 Claims, 1 Drawing Sheet

ELECTROSURGICAL INSTRUMENT FOR EAR SURGERY

This invention relates to an electrosurgical instrument for ear surgery, and in particular, for use in a myringotomy procedure.

BACKGROUND OF THE INVENTION

A myringotomy is a surgical procedure involving an incision of the tympanic membrane that is made to allow ventilation of the middle ear, to permit drainage of middle ear fluid, or to obtain cultures from an infected middle ear. With most older children or adults, it is possible to perform the procedure with a local anesthesia. The known procedure is typically performed with a sharp knife or tympanocentesis needle. This can lead to pain and excessive bleeding, especially if the incision depth exceeds about 2 mm.

SUMMARY OF THE INVENTION

An object of the invention is an improved myringotomy surgical procedure.

We have invented a novel electrode for use in an electrosurgical myringotomy procedure. This electrosurgical procedure using our novel electrode enables physicians to offer to patients a treatment that is efficiently performed, easily learned and thus performed at a significantly reduced price, and with less tissue damage and bleeding compared to procedures done with a knife or needle.

The procedure using our novel electrode is based on performing essentially the same kind of incisions as used heretofore—typically two are common: a wide incision in a circle through the drumhead below an imaginary horizontal line through the inferior tip of the manubrium, or a more limited incision in the anterior or posterior inferior quadrant. However, in accordance with a feature of our invention, the structure of our novel electrode used to make the incision prevents the excision depth from exceeding a safe value. In accordance with another feature of our invention, the electrode of the invention is uniquely configured to enable the active tip to reach via the ear canal passageway and incise the desired tissue while avoiding damage to surrounding tissue.

In a preferred embodiment, our novel electrode is characterized by a straight electrically-insulating portion extending at a certain acute angle to an insulated handle and terminating in an active bare tip portion. The incision is effected with the bare tip moved by the surgeon in a generally arcuate path, and the adjacent portions of the tip support and electrode shaft are made insulating to prevent accidental burns to the patient and to allow the physician to use these insulated parts to help position and guide the active tip portion during the surgical procedure. The electrosurgical procedure has the important advantage of being able to cut the tissue while at the same time coagulating the cut tissue causing minimum bleeding. It is preferred that the electrosurgical currents used be above 2 MHz, and preferably above 3 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
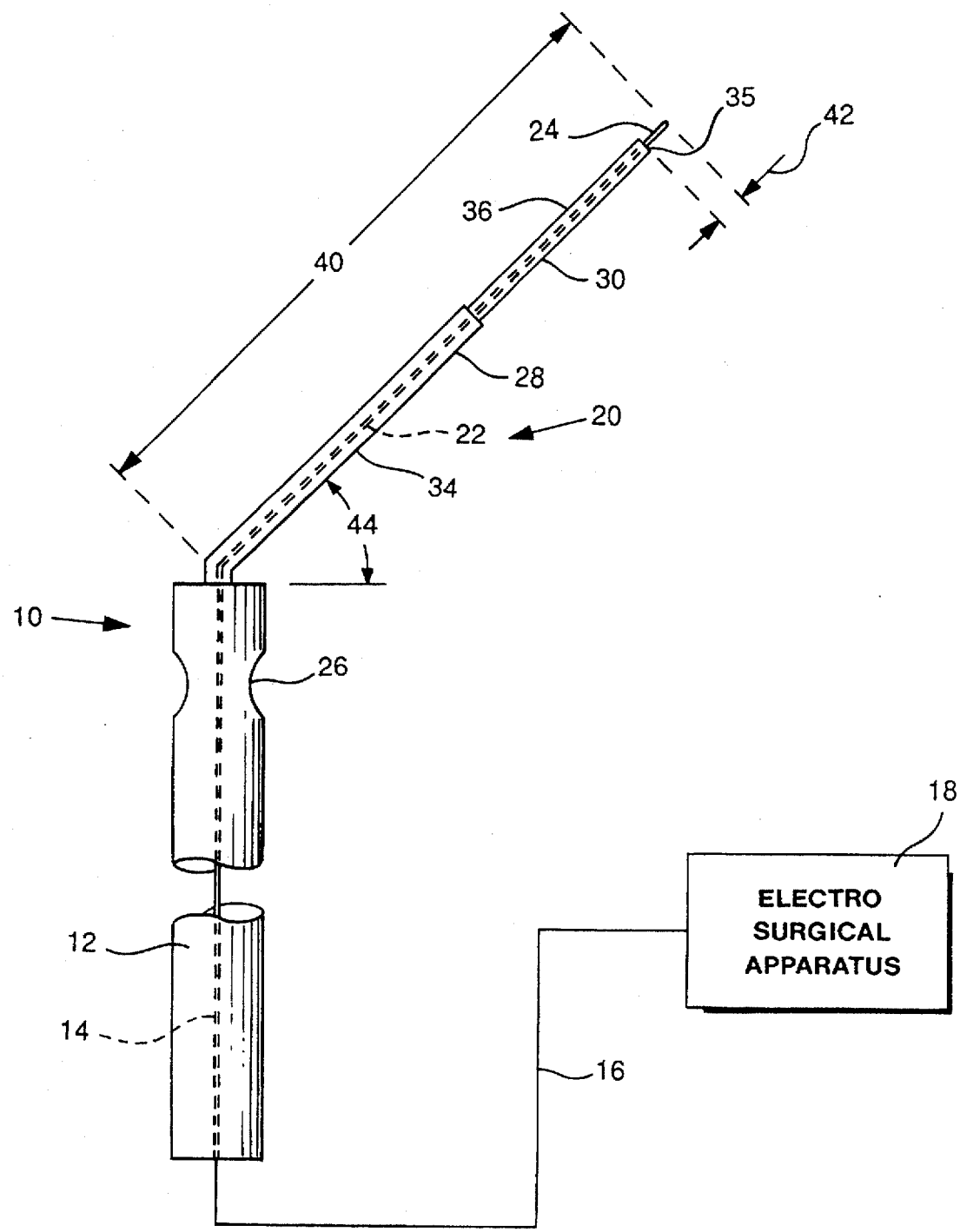
FIG. 1 is a plan view of one form of electrosurgical instrument in accordance with the invention, shown connected to electrosurgical apparatus.

FIG. 1 illustrates a preferred form of the novel electrosurgical instrument 10 of the invention. It comprises an elongated handle 12 of electrically-insulating material having a central electrically-conductive tube or conductor 14 extending throughout its length and connected at its bottom end to a cable 16 which is connected in the conventional manner to conventional electrosurgical apparatus 18. As an example only, the electrosurgical apparatus can be model AAOP Surgitron FFPF available from Ellman International, Inc. of Hewlett, N.Y. The Ellman equipment is preferred due to its high operating frequency, typically above 2 MHz, preferably at 3.8 MHz.

At the opposite end of the handle 12 is mounted an electrosurgical electrode 20 which comprises an electrically conductive tube 22 running lengthwise through it and connected at its end nearest the handle to the electrically-conductive tube 14 and configured to receive and electrically connect to at its distal end the bare metal of a solid wire 24 to which it is bonded, such as by soldering or welding. Also connected to the electrosurgical apparatus 18 is the usual indifferent plate (not shown) which during use is in contact with a patient's body. When the electrosurgical apparatus 18 is energized, high frequency electrosurgical currents are generated which are coupled by way of the cable 16, electrically-conductive tube 14, and electrically-conductive tube 22 to the active, bare, wire end tip 24. The physician, in the usual way, holds the handle 12 while applying the active working end 24 of the electrode to the desired area of the patient to be treated. The handle 12 is provided with dimples 26 as a convenient place for the physician to place his thumb and forefinger for good control of the electrode.

In accordance with a feature of the invention, the electrode portion 20 is constituted of a relatively large diameter section 28 followed by a relatively small diameter section 30 which terminates at the still thinner bare active wire tip 24. The thinner wire tip 24 forms where it meets the section 30 a shoulder 35 which can act as a stop when the electrode is inserted into tissue during the procedure. A typical size of the bare end tip when of tungsten wire, for example, is 0.007 inches.

In accordance with a further feature of the invention, the portion 28 extending from its end adjacent the handle 12 to where it joins the thinner section 30 is covered with a coating 34 of an electrically-insulating material, which may be one of many suitable electrically-insulating rubber or plastic materials. The portion 30 extending from its end adjacent the portion 28 to the active tip 24 is covered with a thinner coating 36 of an electrically-insulating material, which may be one of many suitable thin electrically-insulating plastics, baked Teflon being one example. Thus, the entire length of the electrode 20 from the bare tip 24 to the handle 12 is electrically insulated from the patient. The handle 12, too, is completely electrically-insulated. As an example only, a suitable diameter for the insulated section 30 is about 0.045 inches, which, for the example of the 0.007 inches wire tip 24, produces a shoulder 35 with a radius of about 0.019 inches. This is wide enough to cause the shoulder 35 to act as a stop and prevent the incision depth from exceeding a safe value determined by the length of the wire tip 24. Preferably, the wire tip length does not exceed about 3 mm when using the electrosurgical instrument 10.

The shape of the electrode portion 20, with a generally straight, long, axially-oriented, first portion 28 and with a colinear, thinner second portion 30, ending in the colinear active wire end 24 is critical to achieve the desired object, which is to allow the physician with relative ease to insert the electrode portion 20 into the ear canal and reach the tympanic membrane region desired, activate the apparatus and penetrate the region with the bare tip 24 up to the stop 35, and then move the instrument in the required arcuate path to make the desired arcuate incision without fear of exceeding a safe depth of penetration. The insulating coatings 34 and 36 are essential to prevent accidental burning or other tissue damage by the sides of the electrode as the instrument is manipulated through the aural passageway.

The dimensions of the electrode portion are critical to achieve the desired results. The three most significant dimensions are (1) the overall length of the electrode portion 20, indicated by the reference numeral 40, (2) the length of the bare wire end 24, indicated by the reference numeral 42, and (3) the angle of the electrode portion 20 to the handle 12, indicated by the reference numeral 44. The range of dimensions of the length 40 is about 2.8–3.6 inches, with about 3.2 inches preferred; the range of dimensions of the length 42 of the bare tip is about 0.08–0.13 inches, with about 0.12 inches preferred; the range of angles 44 is about 30°–50° with 40° being preferred. A preferred length for the handle 12, which is not critical, is about 4 inches.

With the Ellman equipment, the fully rectified or cut/coag current is used at a power setting of about 3–4 with the active bare tip electrode 24. There is very little trauma and the sore ear canal area felt by the patient is easily handled by analgesia and anti-inflammatory drugs.

It will also be understood that the electrode of the invention is not limited to its use for a myringotomy procedure. To those skilled in this art, there will certainly be other uses for this novel electrode that provides an active wire tip arranged colinearly to an electrode shaft offset from a carrying handle, with adjacent electrode sections coated with insulating material for accurately guiding and controlling the position of the active tip during a tissue incising electrosurgical procedure.

While the invention has been described in connection with preferred embodiments, it will be understood that modifications thereof within the principles outlined above will be evident to those skilled in the ad and thus the invention is not limited to the preferred embodiments but is intended to encompass such modifications.

What is claimed is:

1. An electrosurgical electrode for incising of tissue, comprising:
   (a) a handle,
   (b) an electrically-conductive shaft member having a first end mounted to the handle and a second end,
   (c) said second end having an active, electrically-conductive, solid tip portion having a bare length of about 2–3 mm terminating in a free end and a first diameter,
   (d) said active tip portion being exposed electrically for applying electrosurgical currents to said tissue when said shaft is connected to a source of electrosurgical currents,
   (e) the portions of said shaft member adjacent said exposed tip portion being electrically-insulating to prevent contact and passage of electrosurgical currents to areas adjacent to or surrounding the tissue to be incised,
   (f) the portions of said shaft member adjacent said exposed tip portion having a larger diameter than the first diameter of said tip portion forming a shoulder spaced from the free end of the tip portion a distance not exceeding about 3 mm and being sufficiently large to act as a stop preventing tissue penetration of the active tip portion beyond its length.

2. An electrosurgical electrode as claimed in claim 1, wherein the active tip portion has a length of about 0.12 inches.

3. An electrosurgical electrode as claimed in claim 1, wherein the shaft portion and the active tip portion have a colinear arrangement.

4. An electrosurgical electrode for incising of tissue, comprising:
   (a) a handle,
   (b) an electrically-conductive shaft member having a first end mounted to the handle and a second end,
   (c) said second end having an active, electrically-conductive, tip portion having a bare length of about 2–3 mm and a first diameter,
   (d) said active tip portion being exposed electrically for applying electrosurgical currents to said tissue when said shaft is connected to a source of electrosurgical currents,
   (e) the portions of said shaft member adjacent said exposed tip portion being electrically-insulating to prevent contact and passage of electrosurgical currents to areas adjacent to or surrounding the tissue to be incised,
   (f) the portions of said shaft member adjacent said exposed tip portion having a larger diameter than the first diameter of said tip portion forming a shoulder sufficiently large to act as a stop preventing tissue penetration of the active tip portion beyond its length,
   (g) the active tip portion having a length of about 0.12 inches,
   (h) the active tip portion having a diameter of about 0.007 inches.

5. In combination:
   a handle having means at one end for connection to electrosurgical apparatus capable of supplying high frequency currents and having at its opposite end means for mounting the electrically-conductive shaft of an electrosurgical electrode and for supplying the high frequency currents to said electrode;
   an electrosurgical electrode for performing surgery on ear tissue, said electrosurgical electrode comprising:
      (a) an electrically-conductive shaft member having a first end mounted to the handle and a second end,
      (b) said second end having an active, electrically-conductive, tip portion having a bare length of about 2–3 mm and a first diameter,
      (c) said active tip portion being exposed electrically for applying electrosurgical currents to said tissue when said electrosurgical apparatus is activated,
      (d) the portions of said shaft member adjacent said exposed tip portion being electrically-insulating to prevent contact and passage of electrosurgical currents to areas adjacent to or surrounding the tissue to be incised,
      (e) means forming a shoulder where said active tip portion meets the adjacent portions of said shaft member, said shoulder being sufficiently wide to prevent tissue penetration of said active tip portion beyond its length, (f) the handle being straight with a central axis and the shaft portion being straight with a central axis that is at an angle of about 30°–50° with respect to the handle.

6. An electrosurgical electrode for incising of tissue, comprising:
  (a) a handle,
  (b) an electrically-conductive shaft member having a first end mounted to the handle and a second end,
  (c) said second end having an active, electrically-conductive, tip portion having a bare length of about 2–3 mm and a first diameter,
  (d) said active tip portion being exposed electrically for applying electrosurgical currents to said tissue when said shaft is connected to a source of electrosurgical currents,
  (e) the portions of said shaft member adjacent said exposed tip portion being electrically-insulating to prevent contact and passage of electrosurgical currents to areas adjacent to or surrounding the tissue to be incised,
  (f) the portions of said shaft member adjacent said exposed tip portion having a larger diameter than the first diameter of said tip portion forming a shoulder sufficiently large to act as a stop preventing tissue penetration of the active tip portion beyond its length,
  (g) the shaft portion having a length between about 2.8–3.6 inches.

7. In combination:
a handle having means at one end for connection to electrosurgical apparatus capable of supplying high frequency currents and having at its opposite end means for mounting the electrically-conductive shaft of an electrosurgical electrode and for supplying the high frequency currents to said electrode;
an electrosurgical electrode for performing surgery on ear tissue, said electrosurgical electrode comprising:
  (a) an electrically-conductive shaft member having a first end mounted to the handle and a second end,
  (b) said second end having an active, electrically-conductive, solid tip portion having a bare length of about 2–3 mm terminating in a free end and a first diameter,
  (c) said active tip portion being exposed electrically for applying electrosurgical currents to said tissue when said electrosurgical apparatus is activated,
  (d) the portions of said shaft member adjacent said exposed tip portion being electrically-insulating to prevent contact and passage of electrosurgical currents to areas adjacent to or surrounding the tissue to be incised,
  (e) means forming a shoulder where said active tip portion meets the adjacent portions of said shaft member, said shoulder being spaced from the free end about 2–3 mm and being sufficiently wide to prevent tissue penetration of said active tip portion beyond its bare length.

8. In combination:
a handle having means at one end for connection to electrosurgical apparatus capable of supplying high frequency currents and having at its opposite end means for mounting the electrically-conductive shaft of an electrosurgical electrode and for supplying the high frequency currents to said electrode;
an electrosurgical electrode for performing surgery on ear tissue, said electrosurgical electrode comprising:
  (a) an electrically-conductive shaft member having a first end mounted to the handle and a second end,
  (b) said second end having an active, electrically-conductive, tip portion having a bare length of about 2–3 mm and a first diameter,
  (c) said active tip portion being exposed electrically for applying electrosurgical currents to said tissue when said electrosurgical apparatus is activated,
  (d) the portions of said shaft member adjacent said exposed tip portion being electrically-insulating to prevent contact and passage of electrosurgical currents to areas adjacent to or surrounding the tissue to be incised,
  (e) means forming a shoulder where said active tip portion meets the adjacent portions of said shaft member, said shoulder being sufficiently wide to prevent tissue penetration of said active tip portion beyond its length,
  (f) the high frequency currents being at a frequency exceeding 2 MHz.

9. A myringotomy surgical procedure for a patient, comprising the steps:
  (a) providing electrosurgical apparatus connected to a handle holding an electrosurgical electrode, said electrosurgical electrode, comprising:
    (i) an electrically-conductive shaft member having a first end mounted to the handle and a second end,
    (ii) said second end having an active, electrically-conductive, tip portion whose active length does not exceed about 3 mm,
    (iii) said active tip portion being exposed electrically for apply electrosurgical currents to said tissue when said electrosurgical apparatus is activated,
    (iv) the portions of said shaft member adjacent said active tip portion being electrically-insulating to prevent contact and passage of electrosurgical currents to areas adjacent to or surrounding the tissue to be incised,
    (v) means forming a shoulder where said active tip portion meets the adjacent portions of said shaft member, said shoulder being sufficiently wide to prevent tissue penetration of said active tip portion beyond its length,
  (b) inserting the electrode into the ear canal until the active tip portion reaches the tympanic membrane tissue of the patient and activating the electrosurgical apparatus,
  (c) penetrating the tissue of the patient until stopped by the means forming a shoulder,
  (d) making an incision with the active tip portion of the electrode.

10. An electrosurgical electrode for incising of tissue, comprising:
  (a) a handle,
  (b) an electrically-conductive shaft member having a first end mounted to the handle and a second end,
  (c) said second end having an active, electrically-conductive, tip portion,
  (d) said active tip portion having a length between about 2–3 mm and being exposed electrically for applying electrosurgical currents to said tissue when said shaft is connected to a source of electrosurgical currents,
  (e) the portions of said shaft member adjacent said active tip portion being electrically-insulating to prevent contact and passage of electrosurgical currents to areas adjacent to or surrounding the tissue to be incised, (f) said active tip portion having a diameter of about 0.007 inches, (g) the portions of said shaft member adjacent said active tip portion having a larger diameter than that of said active tip portion forming a shoulder acting as a stop preventing tissue penetration of the active tip portion beyond its length.

11. An electrosurgical electrode for incising of tissue, comprising:

(a) a handle, (b) an electrically-conductive shaft member having a length between about 2.8–3.6 inches and having a first end mounted to the handle and a second end, (c) said second end having an active, electrically-conductive, tip portion, (d) said active tip portion being exposed electrically for applying electrosurgical currents to said tissue when said shaft is connected to a source of electrosurgical currents, (e) the portions of said shaft member adjacent said active tip portion being electrically-insulating to prevent contact and passage of electrosurgical currents to areas adjacent to or surrounding the tissue to be incised, (f) said active tip portion having a length not exceeding about 3 mm, (g) the shaft portion and the active tip portion having a colinear arrangement, (h) the handle being straight with a central axis and the shaft portion being straight with a central axis that is at an angle of about 30°–50° with respect to the handle.

* * * * *